US 6,469,019 B2

(12) United States Patent
Dib

(10) Patent No.: US 6,469,019 B2
(45) Date of Patent: *Oct. 22, 2002

(54) THERAPEUTIC APPLICATION OF NICERGOLINE

(75) Inventor: Michel Dib, Paris (FR)

(73) Assignee: Aventis Pharma S.A., Antony (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/863,623

(22) Filed: May 23, 2001

(65) Prior Publication Data

US 2001/0044448 A1 Nov. 22, 2001

Related U.S. Application Data

(63) Continuation of application No. PCT/FR99/02867, filed on Nov. 22, 1999.

(30) Foreign Application Priority Data

Nov. 24, 1998 (FR) .............................. 9814793

(51) Int. Cl.[7] ............................... A61K 31/44
(52) U.S. Cl. .................. 514/288; 514/284; 514/285
(58) Field of Search ................ 514/284, 285, 514/288

(56) References Cited

U.S. PATENT DOCUMENTS 3,228,943 A    1/1966  Bernardi et al.
2002/0013332 A1 *  1/2002  Dib et al. ................... 514/288

FOREIGN PATENT DOCUMENTS

EP    0602619    12/1993

OTHER PUBLICATIONS

Medline, DN 85013866, Gallego et al., Paraplegia, (Aug. 1984) 22(4) 216–24 (abstract only).*
Caplus, DN 113:126301, lwasaki et al., Biol. Res. Lab., Tanabe Seiyaku Co., Ltd., Japan Yakuri to Chiro (1990), 18(5), 1995–2004 (abstract only).*
Chem. Abstracts, vol. 107,228784x (1987).
Chem. Abstracts, vol. 118, 225224f (1993).
Chem. Abstracts, vol. 105, 54314k (1986).
Chem. Abstracts, vol. 113, 52358u (1990).
Chem. Abstracts, vol. 111, 108396h (1989).
Chem. Abstracts, vol. 109, 86208c (1988).
Chem. Abstracts, vol. 106, 12788h (1987).
Chem. Abstracts, vol. 115, 198237s (1991).
K. Takahashi, et al: *Br. J. Pharmacol.*, vol. 100, pp. 705–710 (1990).
M. Tanaka, et al: *Neuroscience Letters*, vol. 248, pp. 68–72 (1998).
R.L. Schnaar, et al: *Journal of Neuroscience*, vol. 1(2), pp. 204–217 (1981).
W. Camu, et al: *Journal of Neuroscience Methods*, vol. 44, pp. 59–70 (1992).
A.G. Estevez, et al: *Journal of Neuroscience*, vol. 18(3), pp. 923–931 (1998).
O. Elwan, et al: *Journal of International Medical Research*, vol. 23, pp. 154–166 (1995).
C. Carpene, et al: *J. Pharmacol. (Paris)*, vol. 14(1), pp. 57–66 (1983).

* cited by examiner

*Primary Examiner*—Dwayne C. Jones
*Assistant Examiner*—C. Delacroix-Muirheid
(74) *Attorney, Agent, or Firm*—Balaram Gupta

(57) ABSTRACT

The invention concerns the use of nicergoline for preventing and/or treating motor neuron diseases.

5 Claims, No Drawings

THERAPEUTIC APPLICATION OF NICERGOLINE

This application is a continuation of International application No. PCT/FR99/02867, filed Nov. 22, 1999; which claims the benefit of priority of French Patent Application No. 98/14,793, filed Nov. 24, 1998.

The present invention relates to the use of nicergoline in preventing and/or treating motor neuron diseases.

Nicergoline or (8β)-10-methoxy-1,6-dimethylergoline-8-methanol-5-bromonicotinate (Sermion®) exhibits α-blocking, α2-adrenolytic (CARPENE C. et al., J. Pharmacol, 14, 57–66 (1983)), anti-ischemic (CAHN R. et al., Chem. Abstracts, 107, 228784x (1987); UEDAT et al., Chem. Abstracts, 118, 225224f (1993)), anti-calcium (TAKAHASHI K. et al., Br. J. Pharmacol., 100, 705–710 (1990)), antioxidant (TANAKA M. et al., Neurosci. Let., 248, 67–72 (1998)), and anti-thrombotic (Chem. Abstracts 105, 54314k (1986)) properties, in particular. It improves learning ability and memory (Chem. Abstracts, 113, 52358u (1990); Chem. Abstracts, 111, 108396h, 1989; Chem. Abstracts, 109, 86208c, 1988; Chem. Abstracts, 106, 12788e, 1987; Chem. Abstracts, 115, 198237s, 1991).

It has now been found that nicergoline increases the survival of motor neurons and can thus be used in preventing and/or treating motor neuron diseases.

The motor neuron diseases include amyotrophic lateral sclerosis, progressive spinal muscular atrophy, infantile muscular atrophy and primary lateral sclerosis.

In the presence of trophic support supplied by the neurotrophic factors BDNF or GDNF, motor neuron cultures are composed of large and homogeneous neurons having long branched axons. However, the motor neurons die by apoptosis if the culture is performed in the absence of trophic support.

The effect of nicergoline has therefore been determined in a degeneration model which is induced by depriving cultured motor neurons of neurotrophic factor.

Furthermore, astrocytes play a major role in controlling and maintaining an environment which is suitable for the survival of the motor neurons.

Nicergoline has thus also been tested on a co-culture of motor neurons and astrocytes.

The following protocols were employed:

Motor Neuron-Enriched Cultures

The motor neuron-enriched cultures are prepared using the centrifugation method which was described by R. L. SCHNAAR and A. E. SCHAFFNER, J. Neurosci., 1, 204–217 (1981) and modified by W. CAMU and C. E. HENDERSON, J. Neurosci. Methods, 44, 59–70 (1992) The motor neurons are spread, at a density of 2500 cells per plate, on 35 mm culture plates which have previously been coated with laminin/ornithine in accordance with the method of A. G. ESTEVEZ et al., J. Neurosci., 18 (3), 923–931 (1998). The cultures are then maintained in L15 medium (GIBCO BRL) containing sodium bicarbonate (22 mM), conalbumin (0.1 mg/ml), putrescine (0.1 mM), insulin (5 μg/ml), sodium selenite (31 mM), glucose (20 mM), progesterone (21 nM), penicillin (100 IU/ml) and streptomycin (100 μg/ml).

The motor neurons which are thus obtained consist of large (25–30 μm) and homogeneous neurons which possess long branched axons. More than 70% of the cells are immunoreactive for the neurotrophin p75 receptor and the Islet ½ markers for spinal motor neurons. Approximately 70% of the motor neurons die by apoptosis 24 hours after the spreading if the culture is performed in the absence of a trophic factor.

Cultures of Spinal Cord Astrocytes

The astrocytes are obtained from young, one-day-old rats using the slightly modified method of R. P. SANETO and J. DE VELLIS as described in Neurochemistry a practical approach (A. J. TURNER and H. S. St JOHN) IRL Press, Oxford-Washington D.C., pp. 27–63. The spinal cords are dissected out under sterile conditions and freed of meninges and dorsal ganglia. Five to ten spinal cords are transferred into PBS (phosphate buffer saline) and cut before being incubated at 37° C. for 25 minutes in PBS to which 0.25% trypsin has been added. The enzymatic treatment is stopped by adding 10 ml of Dulbecco's modified Eagle medium (DMEM), to which 10% fetal calf serum (FCS) has been added, and the cells are collected by centrifugation. Another step of mechanical dissociation is performed using the end of a 1 ml pipette. The cells are spread, at a density of $1.5$–$2 \times 10^6$ cells per 25 cm$^2$ of culture medium, in DMEM containing 10% FCS. After 2 days in vitro, the cultures are fed every day. When a visible monolayer of cells has been completed, the cultures are stirred at 250 rpm for 48 hours and, on the following day, the monolayers are treated with cytosine arabinoside ($10^{-5}$ M) for 48 hours. The astrocyte monolayers are then amplified to a density of five on 35 mm culture plates for initially 25 cm$^2$ culture flasks.

The spinal astrocyte cultures consist, to an extent of more than 98%, of flat, polygonal cells which are immunoreactive for the glial fibrillar acid protein (GFAP). The monolayers are exposed to the product to be tested and then incubated with the motor neuron medium in order to obtain a conditioned culture medium. This medium is transferred and tested at different dilutions in order to determine its effects on neuronal survival.

Immunochemistry

The cells are fixed in 4% paraformaldehyde and 0.1% glutaraldehyde in PBS (pH 7.4 and at 4° C. for 15 minutes) and in a cold methanolic solution. The cultures are then washed and the nonspecific sites are blocked with 10% goat serum and 2% bovine serum albumin (BSA) in PBS and treated for immunochemistry using antibodies against the p75 weak affinity neurotrophin receptor or a 200 kD neurofilament protein (Amersham) using the manufacturer's instructions and applying the avidin-biotin-DAB/hydrogen peroxide enhancement reaction.

Treating the Astrocytes with Nicergoline

The astrocytes are treated with nicergoline in the following manner: the product is dissolved in methanol, sterilized by filtration and used immediately after preparation. The treatment which is applied to the enriched motor neuron cultures is effected by adding aliquots of solutions of the products to be tested to the L15 medium by spreading. The astrocyte monolayers are exposed to the vehicle or to the solutions of the compound to be tested for 24 hours and at different concentrations. The astrocyte monolayers are washed 3 times with DMEM and incubated with complete L15 medium. The astrocyte-conditioned medium is recovered 24 hours later and centrifuged at 1800 g for 15 minutes and used immediately or stored at −70° C. for a maximum of 2 weeks without loss of trophic activity.

Counting the Cells and Statistical Analysis

The cells which are immunoreactive for neurofilaments and which exhibit axons which are longer than the diameters of the cells are regarded as being viable motor neurons. The number of motor neurons is estimated by counting the labeled cells in an area of 0.4–1 cm$^2$ under a microscope which enlarges 200 times. In all cases, the values are expressed as a percentage of the number of motor neurons which are present in cultures maintained using trophic factors. The experiments are carried out at least 3 times.

The statistical analyses are performed using the Student's test (t test).

The following results were obtained:

1—Effect of Nicergoline on the Survival of Motor Neurons in Astrocyte/Motor Neuron Co-Cultures

| | % OF LABELED MOTOR NEURONS |
|---|---|
| Vehicle alone | 100 ± 9.4 |
| Nicergoline | |
| 0.1 μM | 115.7 ± 16 |
| 1 μM | 145.5 ± 24* |
| 10 μM | 163.7 ± 22.5** |

*significantly different from the vehicle ($p < 0.05$)
**significantly different from the vehicle ($p < 0.01$)
ND-not determined These results demonstrate that, at a concentration of 10 μM, nicergoline increases the survival of motor neurons by 63.7% as compared with the co-cultures which are treated with the vehicle alone.

2—Neurotrophic-Like Effect of Nicergoline on Neuronal Death in Motor Neuron-Enriched Cultures in the Absence of Trophic Factor In this test, nicergoline increases the survival of the motor neurons by 13% ($p<0.05$).

The present invention also relates to the use of nicergoline for preparing a pharmaceutical which is of use in the treatment of motor neuron diseases, in particular amyotrophic lateral sclerosis, progressive spinal muscular atrophy, infantile muscular atrophy and primary lateral sclerosis.

Nicergoline can be prepared as described in U.S. Pat. No. 3,228,943.

The pharmaceuticals at least comprise nicergoline, either in the pure state or in the form of a composition in which it is associated with any other pharmaceutically compatible product, which may be inert or physiologically active. The pharmaceuticals according to the invention can in particular be employed by the oral route or by the parenteral route.

It is possible to use tablets, pills, powders (gelatin capsules, tablets), oral lyophilisates (Lyoc$^R$) or granules as solid compositions for oral administration. In these compositions, the active principle is mixed with one or more inert diluents, such as starch, tartaric acid, gum arabic, sodium saccharin, vanillin, cellulose, sucrose, lactose or silica under a current of argon. These compositions can also comprise substances other than diluents, for example one or more lubricants such as magnesium stearate or talc, a dye, a coating (sugar-coated tablets) or a varnish.

It is possible to use pharmaceutically acceptable solutions, suspensions, emulsions, syrups and elixirs, containing inert diluents such as water, ethanol, glycerol, vegetable oils or paraffin oil, as liquid compositions for oral administration. These compositions can comprise substances other than the diluents, for example wetting, sweetening, thickening, aromatizing or stabilizing products.

The sterile compositions for parenteral administration can preferably be aqueous or nonaqueous solutions, suspensions or emulsions. It is possible to employ water, propylene glycol, a polyethylene glycol, vegetable oils, in particular olive oil, injectable organic esters, for example ethyl oleate, or other suitable organic solvents, as solvent or vehicle. These compositions can also comprise adjuvants, in particular wetting, isotonizing, emulsifying, dispersing and stabilizing agents. Sterilization can be effected in a variety of ways, for example by aseptic izing filtration, by incorporating sterilizing agents into the composition, by irradiation or by heating. The compositions can also be prepared in the form of sterile solid compositions which can be dissolved at the time of use in sterile water or any other injectable sterile medium.

FORMULATION EXAMPLES

Capsules 5 mg of nicergoline and, as excipients, talc, lactose and magnesium stearate.

Oral Lyophilizate 5 mg of nicergoline and, as excipients, tartaric acid, lactose, gum arabic, sodium saccharin and vanillin.

Powder for Parenteral Use 5 mg of nicergoline and, as excipients, tartaric acid and lactose.

The doses depend on the sought-after effect, on the duration of the treatment and on the administration route employed; they are generally between 30 and 100 mg per day by the oral route for an adult with unit doses ranging from 5 to 20 mg of active substance.

In a general manner, the doctor will determine the appropriate dosage according to the weight and all the other factors peculiar to the subject to be treated.

The invention also relates to the method of treating motor neuron diseases, in particular amyotrophic lateral sclerosis, progressive spinal muscular atrophy, infantile muscular atrophy and primary lateral sclerosis, which method consists in administering nicergoline to the patient.

What is claimed is:

1. A method for the treatment of motor neuron diseases selected from the group consisting of amyotrophic lateral sclerosis, progressive spinal muscular atrophy, infantile muscular atrophy and primary lateral sclerosis, comprising administering to a patient in need of said treatment an effective amount of nicergoline, optionally in combination with a pharmaceutically acceptable carrier.

2. The method of claim 1 wherein said motor neuron disease is amyotrophic lateral sclerosis.

3. The method of claim 1 wherein said motor neuron disease is progressive spinal muscular atrophy.

4. The method of claim 1 wherein said motor neuron disease is infantile muscular atrophy.

5. The method of claim 1 wherein said motor neuron disease is primary lateral sclerosis.

* * * * *